(12) United States Patent
Gately et al.

(10) Patent No.: US 6,452,031 B1
(45) Date of Patent: Sep. 17, 2002

(54) PREPARATION OF TITANIUM ORGANOMETALLIC COMPLEXES COMPRISING A TITANIUM BISALKOXIDE OR DIHALIDE MOIETY

(75) Inventors: Daniel A. Gately, Berthoud; Jeffrey M. Sullivan, Loveland; Karin A. Voll Barclay, Boulder; Dawn A. Arkin, Longmont, all of CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 09/997,302

(22) Filed: Nov. 21, 2001

(51) Int. Cl.⁷ .................................................. C07F 17/00

(52) U.S. Cl. .............................. 556/11; 556/12; 556/53; 526/160; 526/943; 502/103; 502/117

(58) Field of Search .............................. 556/11, 12, 53; 502/103, 117; 526/160, 943

(56) References Cited

U.S. PATENT DOCUMENTS

| | | | | |
|---|---|---|---|---|
| 5,491,246 A | * | 2/1996 | Rosen et al. | 556/11 |
| 5,504,223 A | * | 4/1996 | Rosen et al. | 556/11 |
| 6,255,246 B1 | * | 7/2001 | Devore et al. | 502/118 |

* cited by examiner

*Primary Examiner*—Porfirio Nazario-Gonzalez
(74) *Attorney, Agent, or Firm*—Edward S. Irons

(57) ABSTRACT

Conversion of a ligand of titanium organometallic complex to a titanium bisalkoxy or a titanium dichloride is described.

9 Claims, No Drawings

PREPARATION OF TITANIUM ORGANOMETALLIC COMPLEXES COMPRISING A TITANIUM BISALKOXIDE OR DIHALIDE MOIETY

FIELD OF THE INVENTION

This invention relates to the conversion of cyclopentadienyl compounds to titanium organometallic complexes by treatment with a dialkoxy titanium dihalide.

BACKGROUND OF THE INVENTION

U.S. Pat. Nos. 5,491,246 and 5,504,223 describe the treatment of $Me_4C_5SiMe_2N^t$—$Bu(Li_2)$ with titanium tetraisopropoxide to provide $Me_4C_5SiMe_2N^t$—$BuTi(OiPr)_2$.

It is known to convert certain cyclopentadienyl amines to titanium organometallic complexes including titanium bisalkoxide or dichloride complexes by treatment with titanium tetraisopropoxide and silicon tetrachloride.

No known prior art discloses the use of a dialkoxy titanium dihalide to convert a cyclopentadienyl compound to an organometallic complex that includes a titanium bisalkoxy or dichloride moiety.

Definitions

In this specification, the following expressions have the meanings set forth hereinafter:

(1) Cyclopentadienyl means any substituted or unsubstituted cyclopentadienyl compound group or moiety, including but not limited to any alkylcyclopentadienyl, any indenyl, or alkyl indenyl group, preferably a $C_1$ to $C_5$ alkyl group.

(2) Alkoxide means any radical or group having the formula —OR, wherein R is an alkyl group.

(3) Cyclopentadienyl silyl amine means a compound of Formula

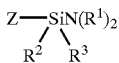

in which Z is a cyclopentadienyl group or moiety and each of $R^1$, $R^2$ and $R^3$ is independently, the same or a different alkyl group, preferably a $C_1$ to $C_{10}$ alkyl group.

(4) Constrained Geometry means that the metal atom in the metal coordination complex and also in the catalyst resulting therefrom is forced to greater exposure of the active catalyst site because of a specific ring structure of a ligand group including the metal atom, wherein the metal is both bonded to an adjacent covalent moiety and held in association with the delocalized π-bonded cyclopentadienyl group through an $\eta^5$ or other π-bonding interaction. It is understood that each respective bond between the metal atom and the constituent atoms of the π-bonded moiety need not be equivalent, that is, the metal may be symmetrically or unsymmetrically π-bound thereto.

SUMMARY OF THE INVENTION

In general, the invention may comprise a process wherein a ligand of a titanium organometallic complex is reacted with dihalo titanium dialkoxide to provide a reaction mixture including a titanium bisalkoxide derivative of said ligand. In an advantageous practice of the invention, the ligand utilized is of a titanium organometallic complex having constrained geometry. The bisalkoxide may be converted to the corresponding titanium dichloride by treatment with a chlorinating agent, e.g., $SiCl_4$, $AlCl_3$ or $BCl_3$.

GENERAL DESCRIPTION OF THE INVENTION

The generic scope of the invention includes any ligand that forms a titanium bisalkoxide when treated with a dihalotitanium dialkoxide of formula $Cl_2Ti(OR)_2$.

The invention also includes a process which comprises reacting, in a non-interfering solvent, a ligand of a titanium organometallic complex with $X_2Ti(OR)_2$, wherein X is a halogen and R is a $C_1$ to $C_5$ alkyl group, wherein a reaction mixture comprising a solution in said medium of a titanium bisalkoxide derivative of said ligand is produced, wherein said ligand is a cyclopentadienyl silyl amine, or wherein said ligand is a ligand of a constrained geometry complex.

The invention may also include the process for producing a titanium bisalkoxide complex which comprises:

(i) treating a lithiated cyclopentadienyl silyl amine with $Cl_2Ti(OR)_2$,
  wherein R is a $C_1$ to $C_5$ alkyl group,
  wherein a first reaction mixture is produced, and
  wherein said first reaction mixture contains a titanium bisalkoxide complex and lithium chloride, and (ii) removing said lithium chloride from said first reaction mixture
  wherein a mother liquor containing a solution of said titanium bisalkoxide complex is produced.

In general, a compound comprising a cyclopentadienyl moiety, typically a silyl amine, is deprotonated with an alkali metal, preferably a lithium alkyl, in a non-interfering medium, e.g., a mixture of hexane and ethyl ether, at a temperature of from about −20° C. to room temperature. The deprotonated cyclopentadienyl compound is treated with $Cl_2Ti(OR)_2$ at an initial low temperature, e.g., −20 to −35° C., which is raised to room temperature over an appropriate time period. The intermediate bis(alkoxy titanate) complex that forms is treated with silicon tetrachloride, boron trichloride, or phosphorous trichloride, preferably at −20 to −35° C., for conversion to the metallocene dichloride. The dichloride may be converted to a metallocene by treatment with diene in the reaction mixture in which it is produced. Optionally, the dichloride may be separated from the reaction mixture prior to conversion. The metallocene complex product is alkali metal free.

EXAMPLE 1

In a first vessel, 1 equivalent of $TiCl_4$ is added to 1 equivalent of $Ti(OiPr)_4$ in hexanes to provide a first reaction mixture that contains $Cl_2Ti(OiPr)_2$

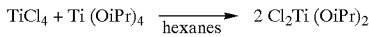

Lithiated 2-methyl indenyl Si(Me)$_2$

is added to the $Cl_2Ti(OiPr)_2$ in situ in the second reaction mixture in which it was formed at room temperature, followed by refluxing for about 2 hours, cooling to room temperature, and filtering to provide a mother liquor that comprises a solution of the intermediate bisisopropoxide in hexanes:

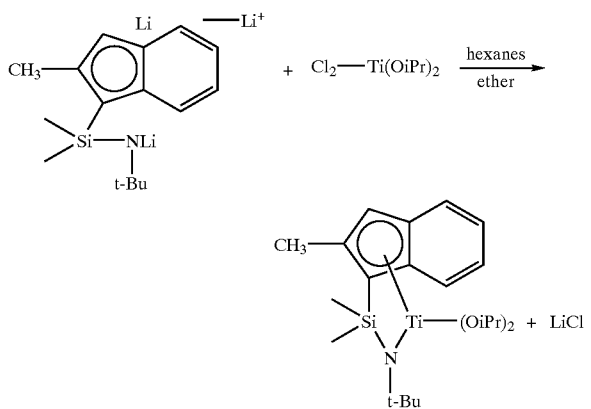

The bisisopropoxide is filtered and then treated in situ with 1.5 eq $SiCl_4$, refluxed for 4 hours, cooled to room temperature, and filtered.

We claim:

1. The method for producing a titanium bisalkoxide complex which comprises
   (i) treating a lithiated cyclopentadienyl silyl amine with $Cl_2Ti(OR)_2$,
      wherein R is a $C_1$ to $C_5$ alkyl group,
      wherein a first reaction mixture is produced, and
      wherein said first reaction mixture contains a titanium bisalkoxide complex and lithium chloride, and
   (ii) removing said lithium chloride from said first reaction mixture
      wherein a mother liquor containing a solution of said titanium bisalkoxide complex is produced.

2. The method of claim 1 further comprising a step
   (iii) treating said step (ii) titanium bisalkoxide complex with silicon tetrachloride
      wherein a second reaction mixture containing a titanium dichloride complex is produced.

3. A process which comprises reacting in a non-interfering solvent a ligand of a titanium organometallic complex with $X_2Ti(OR)_2$ wherein X is a halogen and R is a $C_1$ to $C_5$ alkyl group,
   wherein a reaction mixture comprising a solution in said solvent of a titanium bisalkoxide derivative of said ligand is produced.

4. The process of claim 3 wherein said ligand is a cyclopentadienyl silyl amine.

5. The process of claim 3 wherein said ligand is a ligand of a constrained geometry complex.

6. The method of claim 1 wherein $Cl_2Ti(OR)_2$ in step (i) is $Cl_2Ti(isopropoxide)_2$.

7. The process of claim 3 wherein $X_2Ti(OR)_2$ is $Cl_2Ti(isopropoxide)_2$.

8. The process of claim 3 wherein said ligand of a titanium organometallic complex has the formula

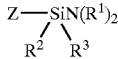

in which Z is a cyclopentadienyl group and each of $R^1$, $R^2$ and $R^3$ is independently the same or a different alkyl group.

9. The process of claim 3 wherein said ligand of a titanium organometallic complex is an unsubstituted or substituted cyclopentadienyl group or an unsubstituted or substituted indenyl group.

* * * * *